United States Patent
Fried et al.

(10) Patent No.: US 11,712,569 B2
(45) Date of Patent: Aug. 1, 2023

(54) SYSTEM AND METHODS OF DECREASING THE DIRECTIONAL SENSITIVITY OF AXIALLY ALIGNED RECHARGEABLE IMPLANT

(71) Applicant: Medtronic, Inc., Minneapolis, MN (US)

(72) Inventors: Andrew Fried, Woodbury, MN (US); Venkat Gaddam, Plymouth, MN (US); Brett Otteson, Minneapolis, MN (US); Mehmet Arcan Erturk, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 300 days.

(21) Appl. No.: 16/948,643

(22) Filed: Sep. 25, 2020

(65) Prior Publication Data
US 2021/0085987 A1    Mar. 25, 2021

Related U.S. Application Data

(60) Provisional application No. 62/905,822, filed on Sep. 25, 2019.

(51) Int. Cl.
| | |
|---|---|
| *A61N 1/372* | (2006.01) |
| *H02J 50/10* | (2016.01) |
| *A61N 1/378* | (2006.01) |
| *H02J 50/80* | (2016.01) |
| *H02J 50/90* | (2016.01) |

(52) U.S. Cl.
CPC ....... *A61N 1/37223* (2013.01); *A61N 1/3787* (2013.01); *H02J 50/10* (2016.02); *H02J 50/80* (2016.02); *H02J 50/90* (2016.02)

(58) Field of Classification Search
CPC .............. A61N 1/37223; A61N 1/3787; A61N 1/37229; H02J 50/80; H02J 50/90; H02J 50/10

See application file for complete search history.

(56) References Cited

U.S. PATENT DOCUMENTS

| | | |
|---|---|---|
| 7,191,007 B2 | 3/2007 | Desai et al. |
| 7,945,334 B2 | 5/2011 | Jimenez et al. |
| (Continued) | | |

FOREIGN PATENT DOCUMENTS

| | | |
|---|---|---|
| EP | 3242721 B1 | 9/2019 |
| WO | WO2016112401 A1 | 7/2016 |
| WO | WO2018096331 A1 | 5/2018 |

OTHER PUBLICATIONS

Yao et al., Evolutionary Beamforming Optimization for Radio Frequency Charging in Wireless Rechargeable Sensor Networks, Aug. 2017, 23 pages, Sensors (Basel, Switzerland). available at https://www.ncbi.nlm.nih.gov/pmc/articles/PMC5579717/.

(Continued)

*Primary Examiner* — Tammie K Marlen
(74) *Attorney, Agent, or Firm* — Patterson Thuente IP

(57) ABSTRACT

The instant application relates to inductive charging of devices subject to migration. Embodiments described herein provide charging to devices at variable depths and locations to accommodate both net displacement of an implantable device as well as angular rotation of the implantable device by selecting appropriate sets or subsets of available field generation coils.

12 Claims, 13 Drawing Sheets

(56) References Cited

U.S. PATENT DOCUMENTS

| | | |
|---|---|---|
| 8,391,991 B2 | 3/2013 | Rahman et al. |
| 8,626,308 B2 | 1/2014 | Meskens |
| 9,700,731 B2 | 7/2017 | Nassif et al. |
| 9,770,596 B2 | 9/2017 | Nassif et al. |
| 9,805,863 B2 | 10/2017 | Hansen et al. |
| 10,350,420 B2 | 7/2019 | Carbunaru et al. |
| 10,478,619 B2 | 11/2019 | Lee et al. |
| 10,603,500 B2 | 3/2020 | Nassif et al. |
| 10,682,521 B2 | 6/2020 | Jiang et al. |
| 10,722,721 B2 | 7/2020 | Nassif et al. |
| 10,729,903 B2 | 8/2020 | Jiang et al. |
| 2010/0259217 A1* | 10/2010 | Baarman ............... H02J 7/0013 320/108 |
| 2011/0295340 A1 | 12/2011 | Rahman et al. |
| 2016/0199657 A1 | 7/2016 | Jiang et al. |
| 2017/0216609 A1 | 8/2017 | Nassif et al. |
| 2018/0140850 A1 | 5/2018 | Linder et al. |
| 2019/0321645 A1 | 10/2019 | Jiang et al. |
| 2019/0379232 A1* | 12/2019 | Lemdiasov .......... H04B 5/0081 |
| 2020/0001094 A1 | 1/2020 | Iyer et al. |
| 2020/0001095 A1 | 1/2020 | Iyer et al. |
| 2020/0078594 A1 | 3/2020 | Jiang et al. |
| 2020/0230427 A1 | 7/2020 | Nassif et al. |

OTHER PUBLICATIONS

Abstract of Matsuki et al., Signal transmission for implantable medical devices using figure-of-eight coils, IEEE Transactions on Magnetics (vol. 32, Issue: 5, Sep. 1996), as available at https://ieeexplore.ieee.org/abstract/document/539510.

\* cited by examiner

SYSTEM AND METHODS OF DECREASING THE DIRECTIONAL SENSITIVITY OF AXIALLY ALIGNED RECHARGEABLE IMPLANT

CROSS-REFERENCE TO RELATED APPLICATIONS

This application claims the benefit of U.S. Provisional Application No. 62/905,822 filed on Sep. 25, 2019, the entirety of which is incorporated herein by reference.

FIELD

This disclosure relates to an implantable medical device and more specifically a rechargeable implantable medical device that produces a medical therapy.

BACKGROUND

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices include neuro stimulators, drug delivery pumps, pacemakers, defibrillators, diagnostic recorders, and cochlear implants. Some implantable medical devices provide therapies with significant power demands. To reduce the size of the power source and to extend the life of the power source, some of these implantable devices can be recharged while implanted with a transcutaneous recharge signal produced by one or more field-producing coils external to the patient.

Implantable medical devices configured for recharging are typically configured with either the recharging coil internal to the medical device housing, external to the housing, or remotely located away from the housing. However the medical device recharging coil is configured, it is desirable to improve recharging efficiency for benefits such as decreased recharging time and decreased medical device temperature rise while recharging.

For the foregoing reasons there is a need for a rechargeable implantable medical device with improved recharging efficiency.

SUMMARY

The techniques of this disclosure generally relate to improvements in recharging of implantable devices.

In one aspect, the present disclosure provides a device for remote charging. The device includes a plurality of charging coils and a power supply coupled to all of the plurality of charging coils. A switch matrix connects the power supply to the charging coils and a first subset of the charging coils associated with a first charging zone are powered, creating a corresponding magnetic field. A second subset of the plurality of charging coils associated with a second charging zone can be powered to generate a different magnetic field. A processor is included within the device and is configured to define the first subset of the plurality of charging coils and the second subset of the plurality of charging coils based upon a received charge current, a threshold, and a level of hysteresis.

In another aspect, a system is disclosed that includes an implantable medical device and a device for remote charging. The implantable medical device defines a depth and an angle of orientation with respect to the device for remote charging. The device for remote charging includes a plurality of charging coils, a power supply coupled to all of the plurality of charging coils, a switch matrix connecting the power supply to the plurality of charging coils such that a first subset of the plurality of charging coils associated with a first charging zone are powered and a second subset of the plurality of charging coils associated with a second charging zone are powered, and a processor configured to define the first subset of the plurality of charging coils and the second subset of the plurality of charging coils based upon a received charge current, a threshold, and a level of hysteresis. The processor is configured to select the first subset of the plurality of charging coils and the second subset of the plurality of charging coils based upon the depth and the angle of orientation.

In another aspect, a method for charging an implantable device includes powering a first subset of a plurality of charging coils via a switch matrix, receiving a charge current level via a telemeter indicative of a pairing quality between the first subset of the plurality of charging coils and the implantable device, determining whether the charge current exceeds a threshold minus a hysteresis level, selecting a second subset of the plurality of charging coils based upon a determination that the charge current does not exceed the threshold minus the hysteresis level, and repeating the method steps with the second subset of the plurality of charging coils instead of the first subset of the plurality of charging coils.

In another aspect, a device for remote charging includes a charging coil, a power supply coupled to the charging coil, and a motor coupled to the charging coil and configured to move the charging coil to create a corresponding magnetic field direction. A processor is configured to operate the motor based upon a detected charge current level of a corresponding implantable device and a threshold.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, rechargeable implantable devices that require electricity are charged by the application of an electromagnetic field to the device. The appropriate amount and direction of field used to charge the device varies based upon the orientation and type of the device itself, and in particular the orientation and type of receiver coil contained in the implantable device. Commonly used receiver coils are ferrite surrounded by a coil of conductive material, which is in turn electronically coupled to power storage.

Typical implantable devices receive power for some period of time, and then operate solely on battery power until the next recharging. It is generally desirable for the period of time for charging to be as short as possible, and the amount of operation time before recharging is required to be as long as possible. There are multiple factors that can be modified to achieve these results, such as battery size, materials used, and efficiency of the devices themselves. One factor that cannot be precisely controlled by a medical device manufacturer, however, is the orientation of the device after it is implanted into a patient.

The reasons that this cannot be controlled precisely are varied. First, the medical device may not be implanted in the patient in an exact orientation prescribed by the device manufacturer. Second, implanted devices may migrate over time, both with respect to exact position and with respect to orientation. This migration, even if it is only a few degrees off-axis or a few millimeters in position, can cause variation from the ideal charging conditions.

Figure 1:
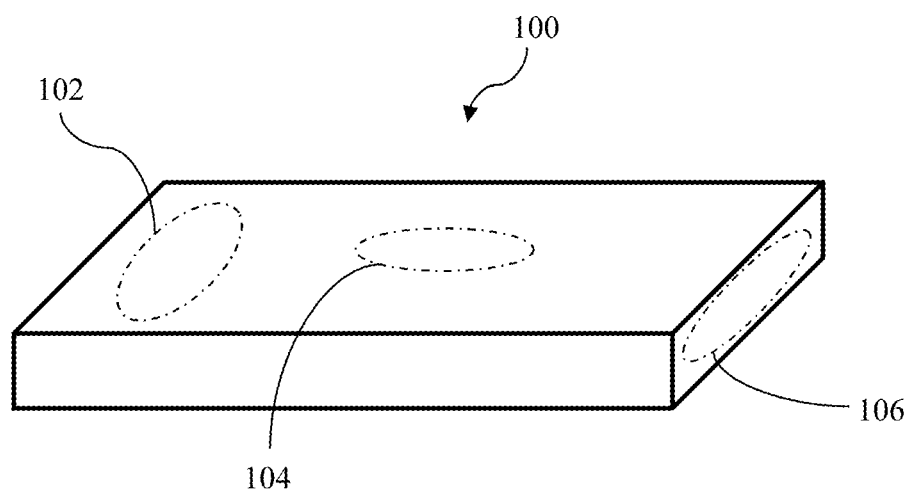
FIG. 1 is a simplified schematic view of an implantable device depicting possible receiving coil locations.

FIG. 1 depicts a simplified, rectilinear implantable device 100. Device 100 can have a receiver coil arranged at various locations, indicated as regions 102, 104, and 106. At any of these regions 102, 104, 106, a receiver can be arranged either inside of or on the outer surface of device 100. The choice of where to position the receiver coil has a direct impact on the type of charging field that will be the most effective. Specifically, the magnetic field should be strongest at, and oriented along the primary axis of, the receiving coil. Charging via a receiver coil arranged in an "up-down" orientation (referring to the orientation of the page) at region 104 is best accomplished by a similarly-oriented field targeted to the center of the device. Charging via a receiver coil arranged in either of the other two regions 102, 106 shown in FIG. 1 is best accomplished with a field that goes front-to-back (referring again to the orientation of the page). In an embodiment, device 100 may include two or more recharging coils, for example located at two or more of regions 102, 104, 106 or other.

It should be understood that one or more receiving coils can be arranged at almost any location in an implantable device, and that the devices themselves often incorporate more complex geometries than a rectilinear box. The two primary directions for best charging, however, are those described above (i.e., either parallel to or orthogonal to the plane along which the device primarily extends).

Figure 2:
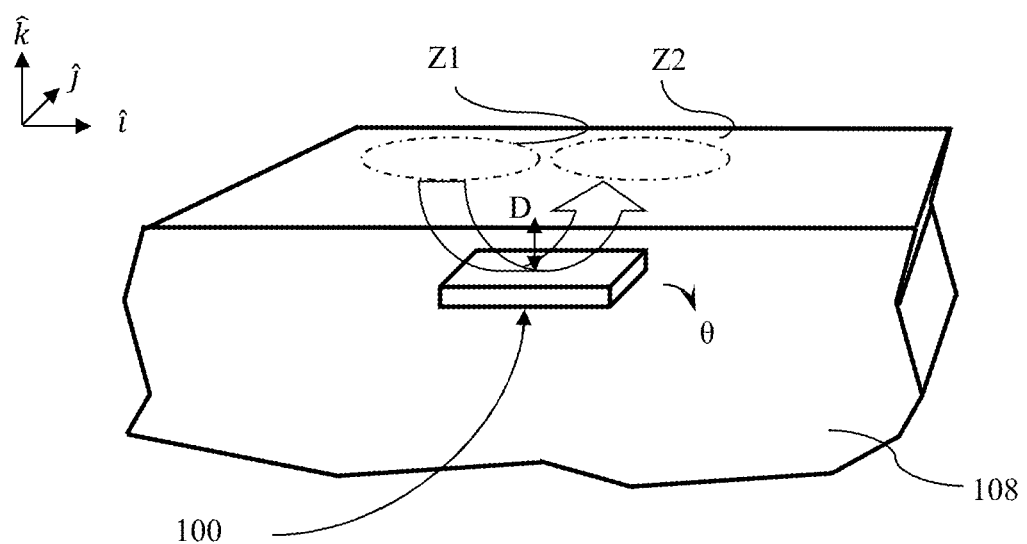
FIG. 2 is a cutaway view of an implanted device depicting charging field directions.

As shown in FIG. 2, the "front-to-back" charging orientation, or the orientation that is parallel to the plane along which the device primarily extends, typically requires providing a magnetic field that is parallel to the skin of a patient. This field is shown by the hollow arrow in FIG. 2 connecting zone Z1 and zone Z2 on the patient's body. The device 100 can be implanted in a patient's body 108 at a depth D, at an angle θ away from perfectly parallel to the skin. The angle θ and the net displacement of the device over time can have components in any of the i, j, or k directions indicated by the coordinates in the drawing.

The field shown by the open arrow may become less effective or even completely ineffective for charging the device 100 over time. This can be caused by migration of the device 100 to a different depth D where the field is not strong enough, for example. Similarly, the device 100 could migrate to an angle that is off-axis with the field (as shown in FIG. 2, θ=0). Rotation of device 100 can reduces the magnetic flux at the charging coil by a dot product of the field direction and the charging coil's orientation direction.

The instant application solves the problem of reduction of recharge efficiency due to implantable device migration and rotation, in a way not previously contemplated. Specifically, the embodiments described herein provide variable depth and location of magnetic field to accommodate both net displacement of the device as well as angular rotation of the device by selecting appropriate sets or subsets of available field generation coils. Solutions described herein solve these problems in the design of the external charging systems using coil windings which produce adjacent loops of current flowing in opposite directions. This increases the radial component of the field directly between the two coils at a given depth. An array of such coils can be produced, for example in an intertwined fashion (similar to gravure pattern). An array of independent coils can be connected to a switch matrix which allows coils to be connected in series or in parallel to produce a desired effect. An algorithm could be used to switch the direction of radial field by changing which coils are activated and maintain charging through the most efficient available coils. Orthogonal coils designed in a cylindrical fashion could be employed. A single coil oriented horizontally could be employed and connected to a mechanical rotational mechanism or motor to change the direction of the field.

Figure 3A:
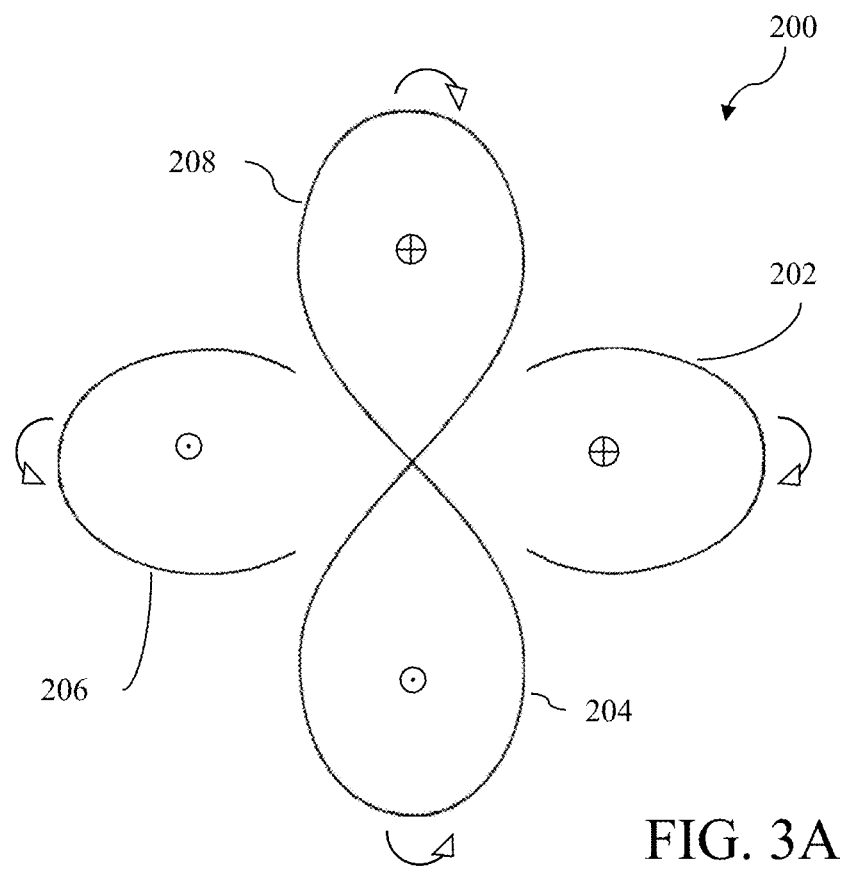
FIGS. 3A and 3B depict a charging field generation design and a corresponding magnetic field line, according to an embodiment.
Figure 3B:
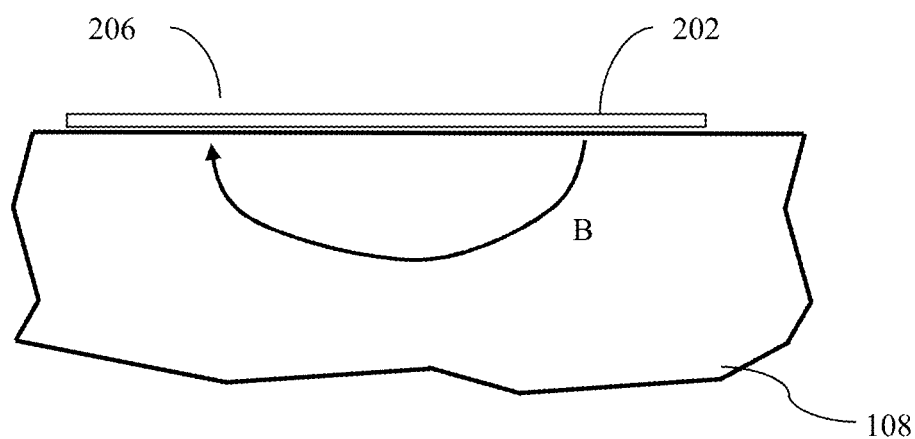

FIG. 3A depicts a field generation device 200 according to a first embodiment that has a "cloverleaf" pattern. Field generation device 200 includes four coils 202, 204, 206, and 208. The coils of field generation device 200 are wired in two pairs, such that a single power supply (not shown) can provide current to either the first pair (made up of coils 202 and 206) or the second pair (made up of coils 204 and 208). As depicted by the magnetic field indicators within each of the four coils 202, 204, 206, and 208, each pair generates two opposite magnetic fields, one into the page and one out of the page. FIG. 3B shows the resulting magnetic field B in the patient's body 108 when the first pair is powered.

As can be seen from FIGS. 3A and 3B, the choice of which pair of coils to power will have a direct effect on the field direction. In the embodiment shown in FIG. 3A, the field direction can be shifted 90° simply by selecting the other pair of coils. An operator could therefore determine which pair of coils was more effective at charging an implanted device, and operate using that pair, without any manual movement of the device itself. Furthermore, because the pairing of emitter and receiver coils can be detected from a level of impedance, systems are envisioned (and described in more detail below) in which the operator need not make any determination of which coil to use, as the device may autonomously determine which pairs are best suited for the desired level of charging.

Figure 4:
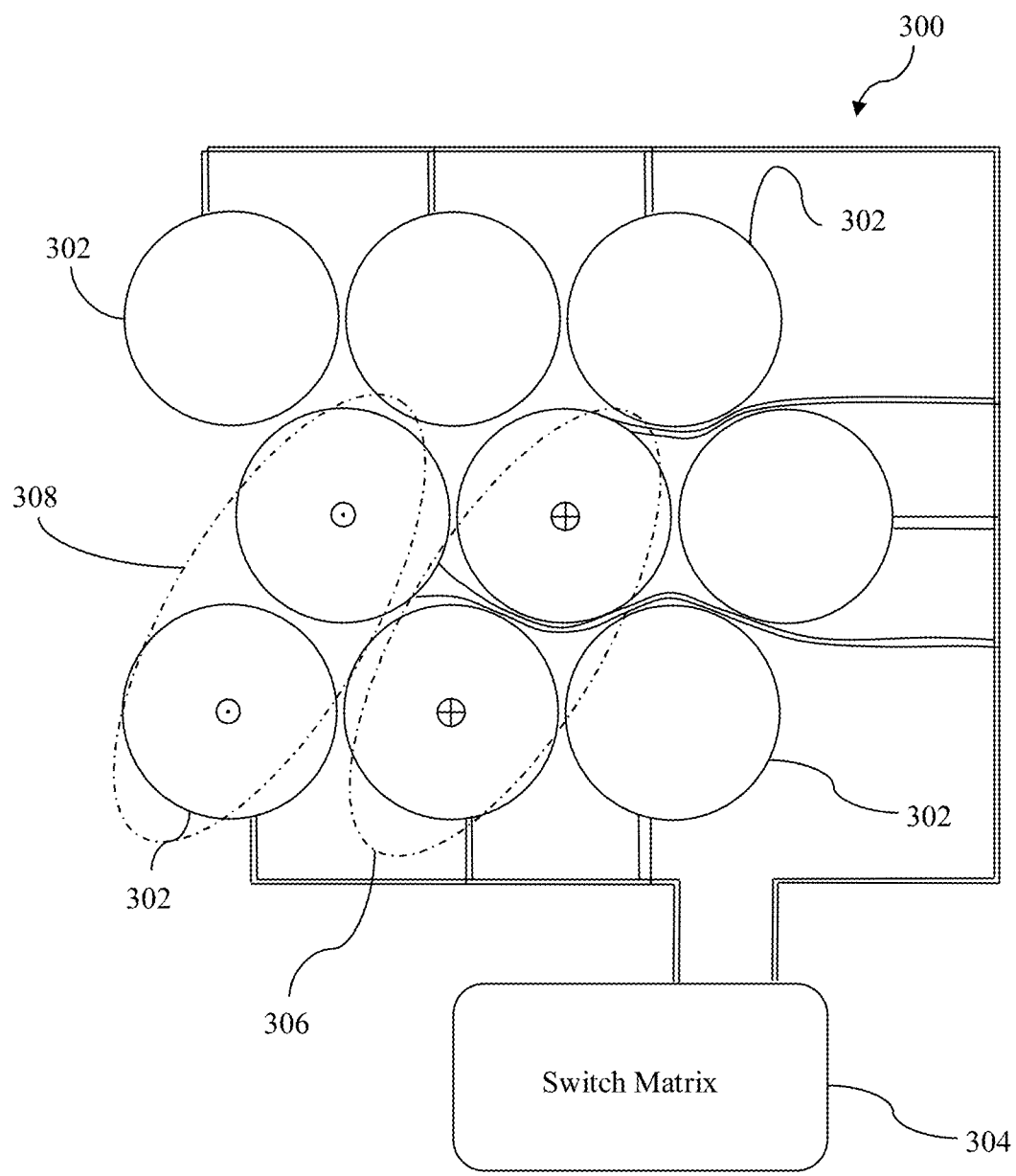
FIG. 4 is a multi-coil field generation design according to an embodiment.

FIG. 4 is a more complex version of the design depicted in FIG. 3. Specifically, while FIG. 3 depicted two pairs of coils at right angles, FIG. 4 shows a field generation device 300 that includes an array of circular coils 302, each capable of being driven by a switch matrix 304 to create either a field into the page our out of the page. As shown in FIG. 4, two of the coils are driven to create a field into the page, while two other coils are driven to generate a field out of the page. The net effect is a first zone 306 and a second zone 308, which correlate to the start and end points of magnetic field lines that can be directed into a patient, respectively, as previously described with respect to FIG. 3B.

Figure 5:
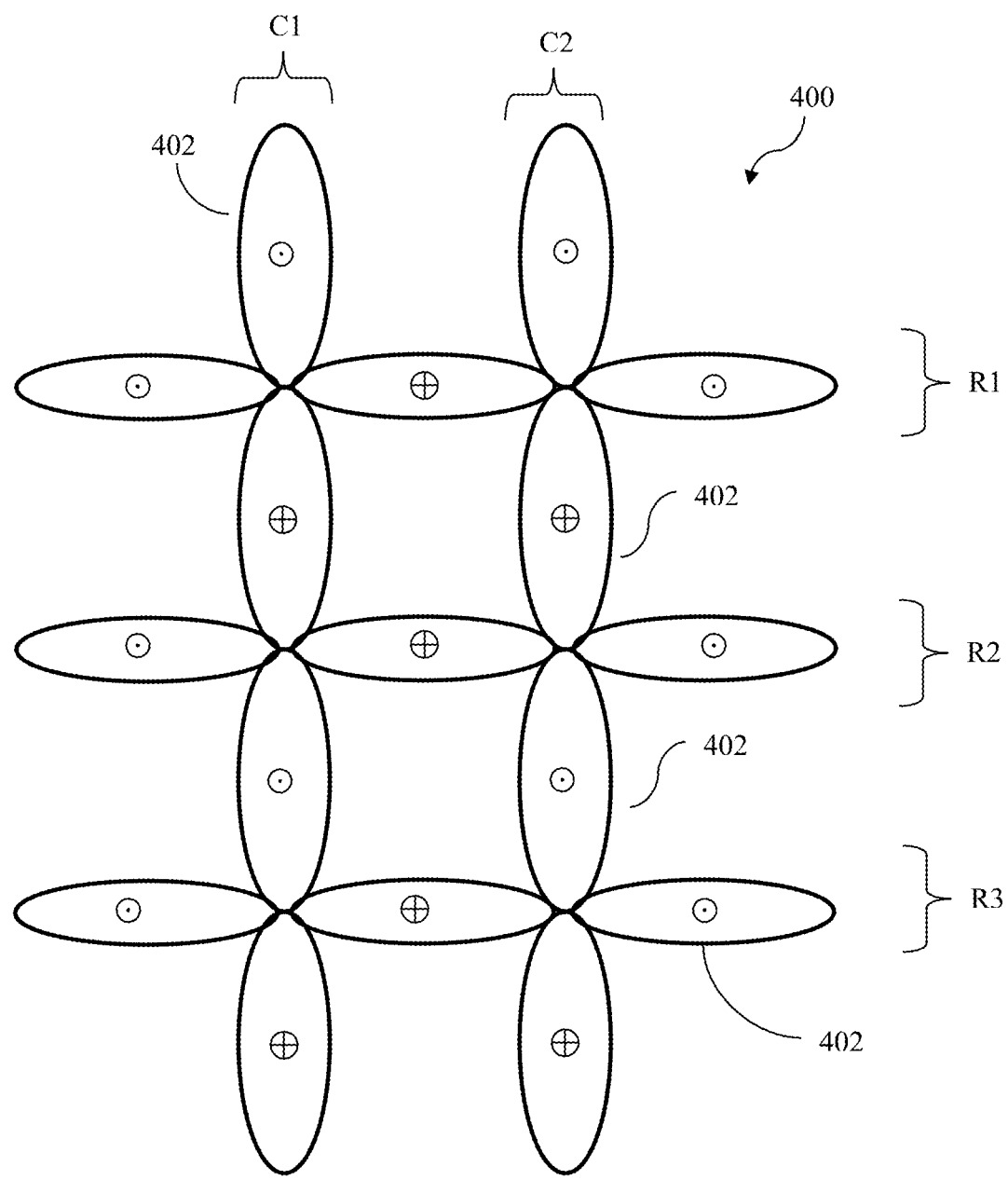
FIG. 5 is a multi-coil field generation design according to an embodiment.

FIG. 5 depicts yet another embodiment of a field generation device 400, in which rows and columns of coils 402 can be operated together. For example, a power source (not shown) could provide power to any of the first, second, or third rows R1-R3, either simultaneously or separately. Likewise, first and second columns C1 and C2 can be powered either simultaneously or separately from both one another and from the various rows. In embodiments, a grid of such rows and columns could be created that is spread into a fabric or mesh. The rows and columns of such a fabric can be selected and operated to charge an implanted device no matter where relative to the center of the fabric the device had migrated.

Figure 6:
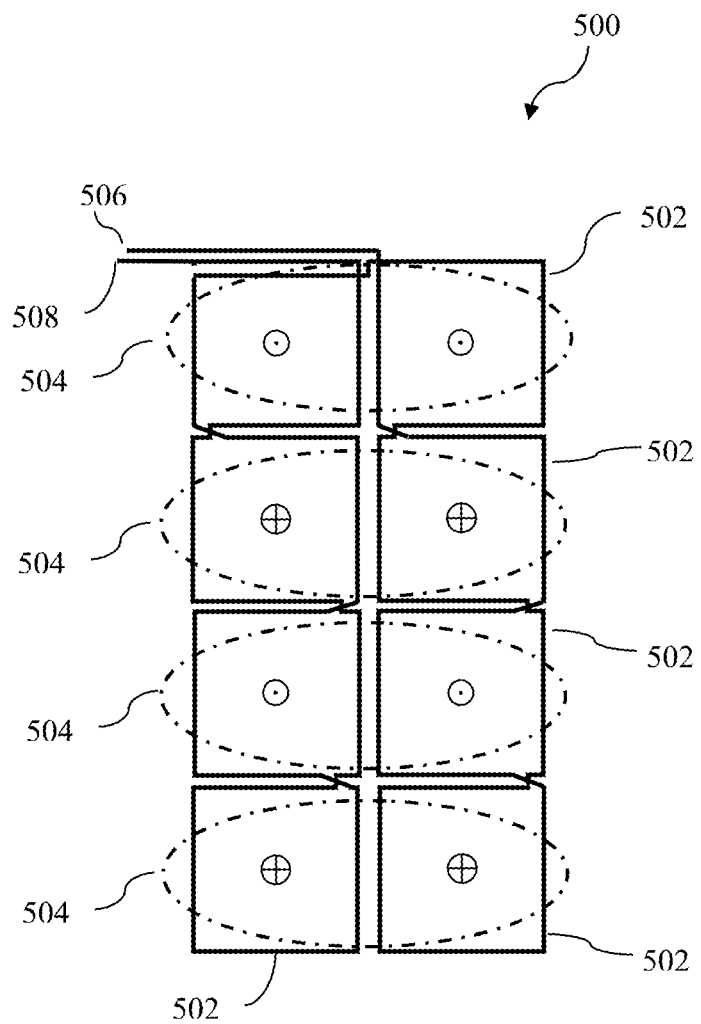
FIG. 6 is a multi-coil field generation design according to an embodiment.

FIG. 6 is another embodiment of a field generation device 500, in which a single power supply can be used to power coils 502 that generate alternating magnetic field regions 504 using a single power supply at anode 506 and cathode 508 leads. As described above with respect to FIG. 5, a fabric of such coils could be generated that has a large number of such coils 502 to charge a device found anywhere adjacent the fabric.

Figure 7:
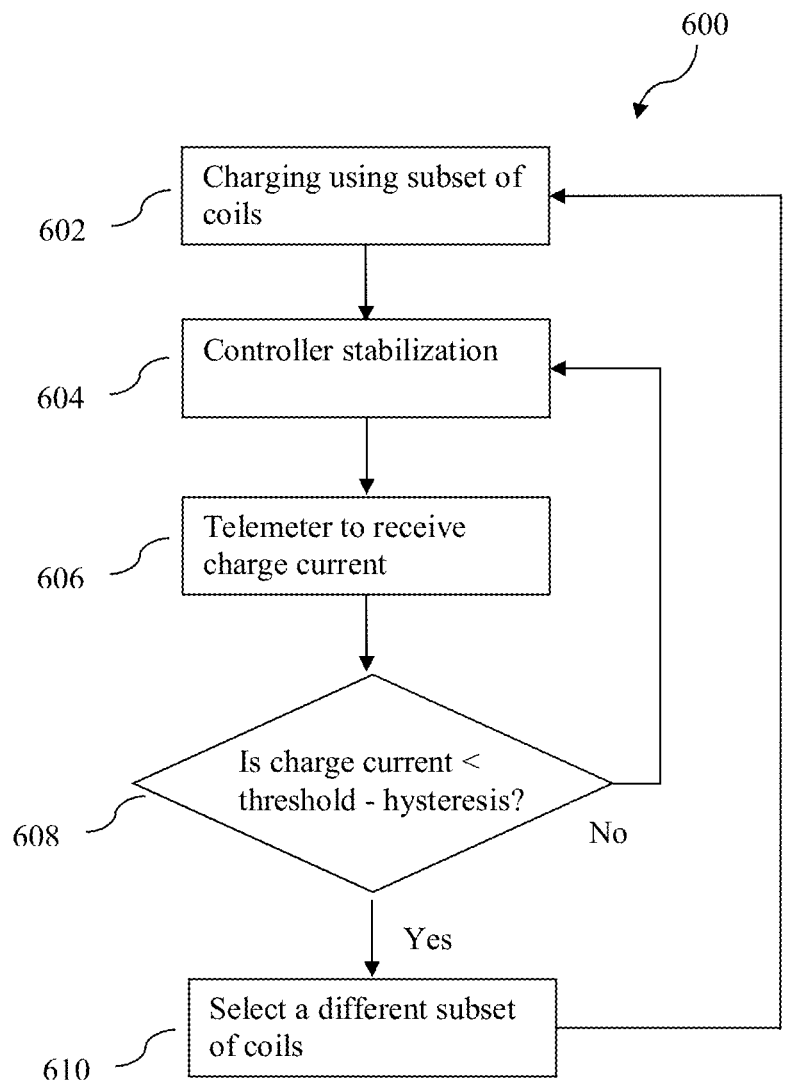
FIG. 7 is a flowchart of a method for operating a multi-coil field generation design.

FIG. 7 is a flowchart depicting a method 600 for selecting coils to be used, according to an embodiment. As described with respect to FIGS. 1-6, in general it is better to charge rapidly by increasing charge current. As shown in FIG. 7, charging begins at 602 with a subset of coils powered. The choice of initial coils to power can be made based on previous charging sessions, based on user input, based on an expected location, depth, and orientation of the device, or even randomly.

With respect to the embodiment depicted in FIG. 3, the subset of coils that are powered at 602 could be one of the two pairs (202 and 206, or 204 and 208), for example. Similarly, with respect to the embodiment depicted in FIG. 4, the subset of coils powered at 602 could be two or more of the coils 302, with some of the coils 302 directing magnetic flux into the page and some of the coils 302 directing flux out of the page to create zones 308. With respect to the embodiment depicted in FIG. 5, the subsets selected at 602 could be individual rows, columns, or combinations thereof.

At 604, the controller is stabilized. Controller stabilization 604 allows the magnetic field to reorient and charging to begin. As charging begins, an implanted device begins receiving charge current, which can be detected and reported back to the charging device at 606. At 608, the reported level of charge current from the implanted device is compared to a threshold and the hysteresis effect of any recent switch in the subset of coils. This determination can be made by a processor (not shown). The threshold can be set for a particular device, or in some embodiments the threshold can be determined based on past charging sessions, or based on operation of the method 600 with a different set of coils selected at 602. In any event, if the charge current exceeds the threshold (minus any hysteresis effect), then charging continues as indicated by the "No" arrow of the method 600. If, however, the charge current is less than the threshold (minus any hysteresis effect), then a different set of coils is chosen at 610 as indicated by the "Yes" arrow of the method 600.

The method 600 can be used iteratively, and as better subsets of coils are detected the threshold can be modified accordingly. In embodiments, different subsets of coils can be selected at 610 based on a timer, such that even if acceptable levels of charging have been established the method 600 would still search for other subsets that would charge even more rapidly.

Additionally, changing between pairs that provide sufficient levels of charging can reduce localized heating. Heating can be reduced by alternating between coils or sets of coils, which allows more rapid charging through each than would otherwise be possible (because doing so without alternation would exceed the maximum heating that is acceptable).

Figure 8:
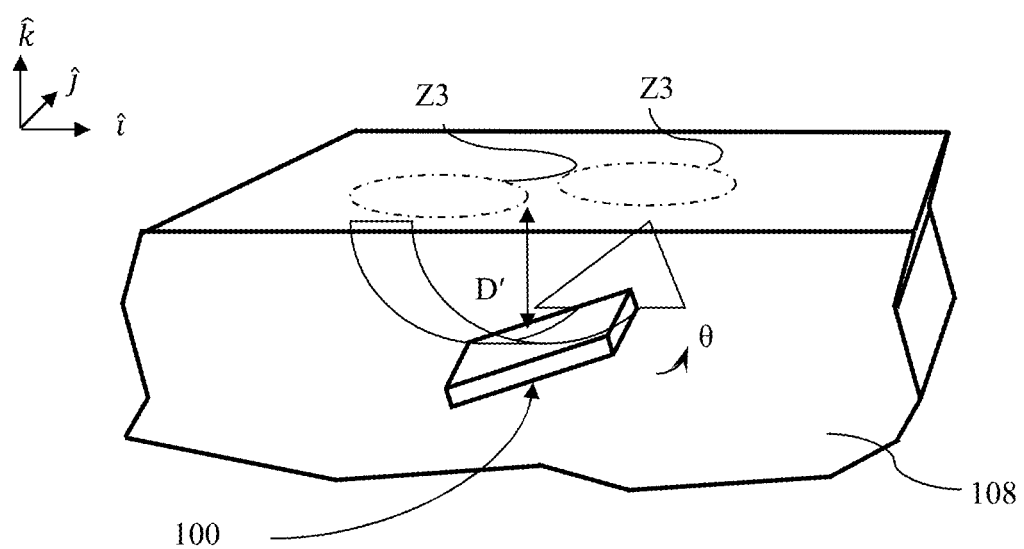
FIG. 8 is a cutaway view of an implanted device depicting charging field directions.

Notably, while FIGS. 1-6 show the activated coils as being adjacent to one another, they could be spread apart more widely, or (as shown in FIG. 3) they could be used in concert with another to create differently shaped and sized charging zones. This is particularly important when, as shown in FIG. 8, the device 100 has rotated relative to the patient's skin (i.e., θ>0). When the device 100 is rotated, the optimal field (shown by the open arrow in FIG. 8) may be at a different depth D' compared to the initial depth D described in FIG. 1. As a result, the ideal zones Z3 and Z4 at which magnetic field is directed into and out of the patient's body for charging the device are spaced further apart and offset, as compared to the zones Z1 and Z2 depicted and described above with respect to FIG. 2. Likewise, the ideal field strength for the magnetic field at zones Z3 and Z4 in FIG. 8 can vary compared to the ideal field strength when the same device 100 is oriented as shown in FIG. 2. By selecting different coils or sets of coils as described in the method of FIG. 7, the location of the zones and the field strength can better approximate the ideal charging conditions. Furthermore, using the method of FIG. 7 in combination with the coil designs of FIGS. 3A-6 provides for better approximations of these ideal charging conditions without any physical movement of the charging device, as required by many conventional systems, and can therefore be more easily automated by a processor or built-in logic system.

Figure 9:
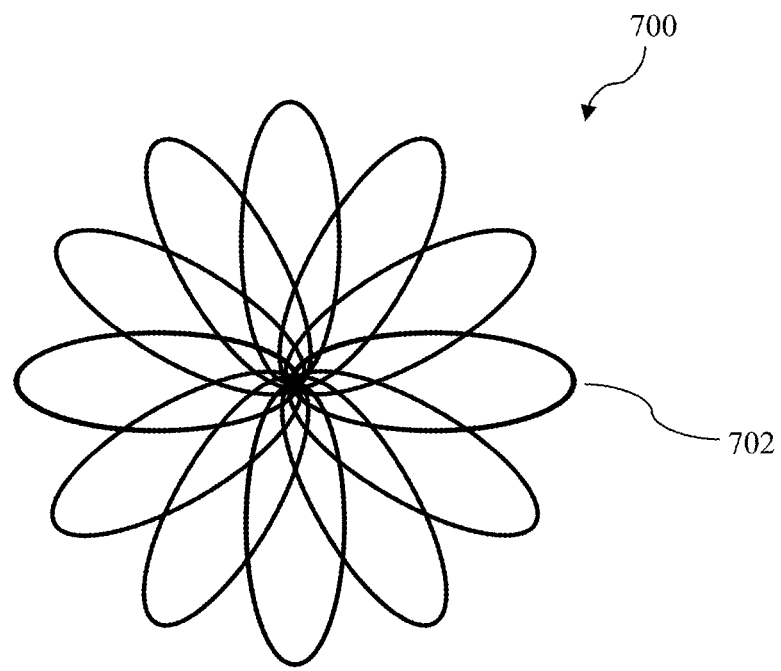
FIG. 9 is a multi-coil field generation design according to an embodiment.

It should be understood that the coil designs depicted in FIGS. 3A-6 are not the only ones that provide these benefits. As shown in FIG. 9, a field generation device 700 that is similar to the one described earlier in FIG. 3A in that it also has a cloverleaf pattern, but having a relatively larger number of coils 702, can be used. In FIG. 9 there are twelve coils in all, and they can be driven in pairs as described with respect to FIG. 3A. By providing more coils, the number of possible angles is increase. In other words, while there are two "charging lanes" associated with the two pairs of coils in FIG. 3A, there are six "charging lanes" associated with the six pairs of coils in FIG. 9, and accordingly the furthest off-axis the ideal charging direction can be from a charging lane is reduced from 45° in FIG. 3A to 15° in FIG. 9.

Figure 10:
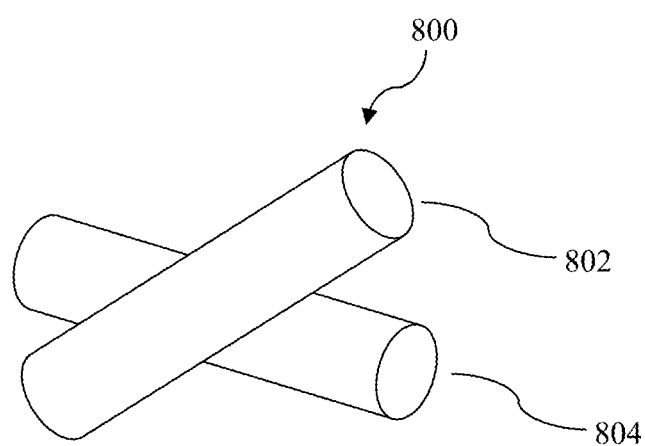
FIG. 10 is a directionally adjustable field-generation design according to an embodiment.

FIG. 10 is another embodiment of a field generation device 800, in which two ferrite rods 802, 804 are arranged along non-parallel axes. The ferrite coils can be wrapped in conductive coils (not shown) to generate an electromagnetic field based on their direction of orientation. In embodiments, a motor (not shown) could be used to rotate a single-rod embodiment, or to rotate one rod 802 with respect to the other 804, to create a desired field direction and strength. Referring to the method of FIG. 7, selecting a subset of coils at 602 or 610 would instead involve rotating one or both of the ferrite rods 802, 804.

Figure 11A:
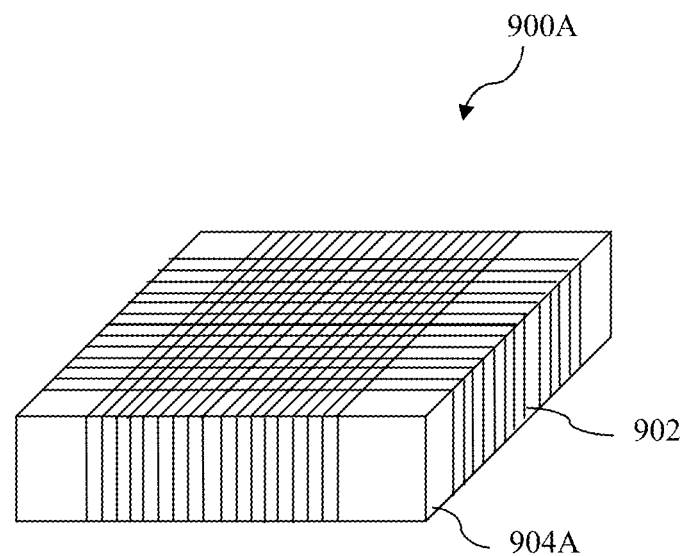
FIGS. 11A and 11B are directionally adjustable field-generation designs according to two embodiments.
Figure 11B:
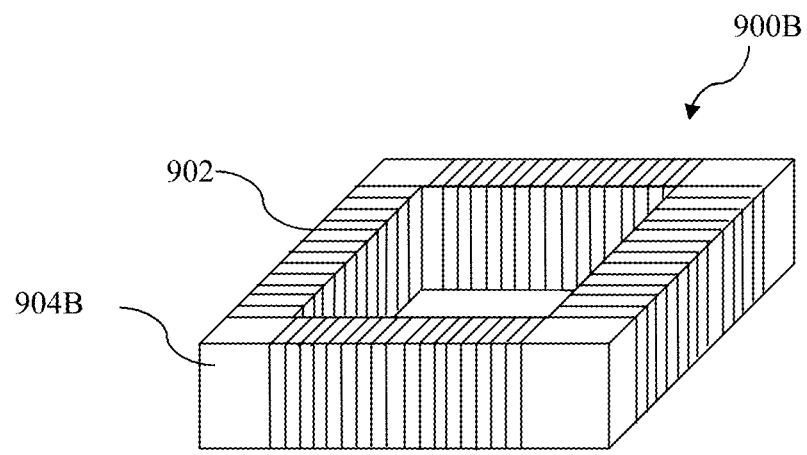

FIGS. 11A and 11B depict two embodiments of a field receiving device, 900A and 900B, respectively. The devices 900A and 900B can be stationary and the coils 902 are wrapped around a core (904A, 904B). FIG. 11A depicts a simpler design in which the core 904A is a solid ferrite block, while FIG. 11B depicts a more complex design in which the core 904B has four separate legs arranged in a square. By wrapping the cores 904A, 904B in coils, fields can be detected that originate from different directions. Alternatively, the cores 904A and 904B wrapped in coils can be used as field generators in some embodiments.

Figure 12:
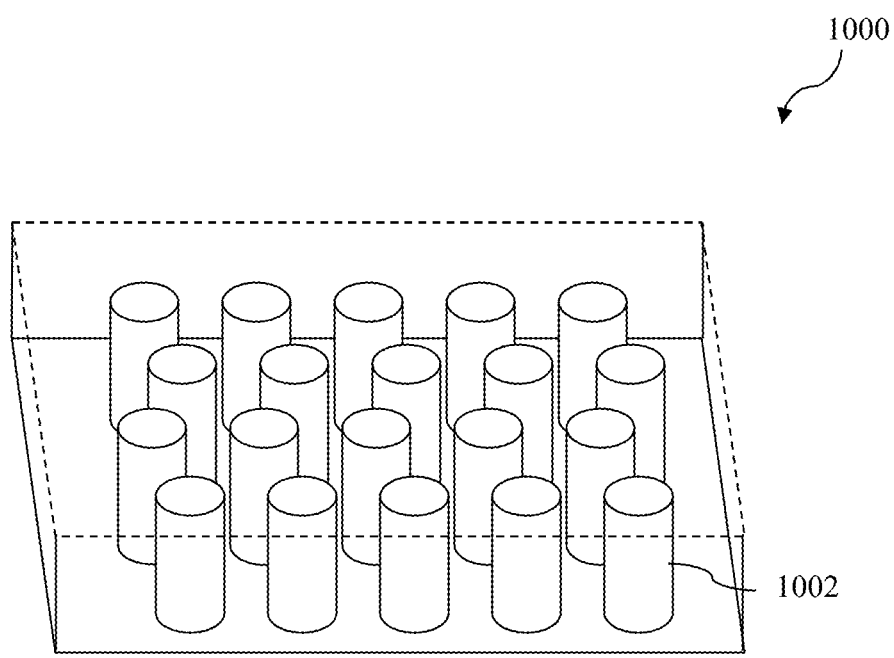
FIG. 12 is a multi-coil charging device according to an embodiment.

It should be understood that by using more complex patterns of cores, such as those with upright "pegs" arranged in a grid and each wrapped in separately-controllable coils 1002 as shown in the charging device of FIG. 12. These and other designs that generate fields starting and ending at different points based on a selected coil or set of coils are contemplated, to provide charging that better approximates the ideal field strength and direction for a device based on its orientation or depth.

Embodiments of the present disclosure may be used with a variety of implantable medical devices, including but not limited to nerve stimulation devices (also known as neuro stimulators or neuromodulation devices), drug delivery pumps, cardiac pacemakers, defibrillators, or implantable cardioverter-defibrillators. In embodiments, neuromodulation devices may be used to stimulate a variety of nerves or associated tissues for treating a variety of conditions. Electrical stimulation may be delivered for spinal cord stimulation (SCS), peripheral nerve stimulation (PNS), peripheral nerve field stimulation (PNFS), deep brain stimulation (DBS), cortical stimulation (CS), pelvic floor stimulation, sacral nerve stimulation, tibial nerve stimulation, gastric stimulation, and the like.

Figure 13A:
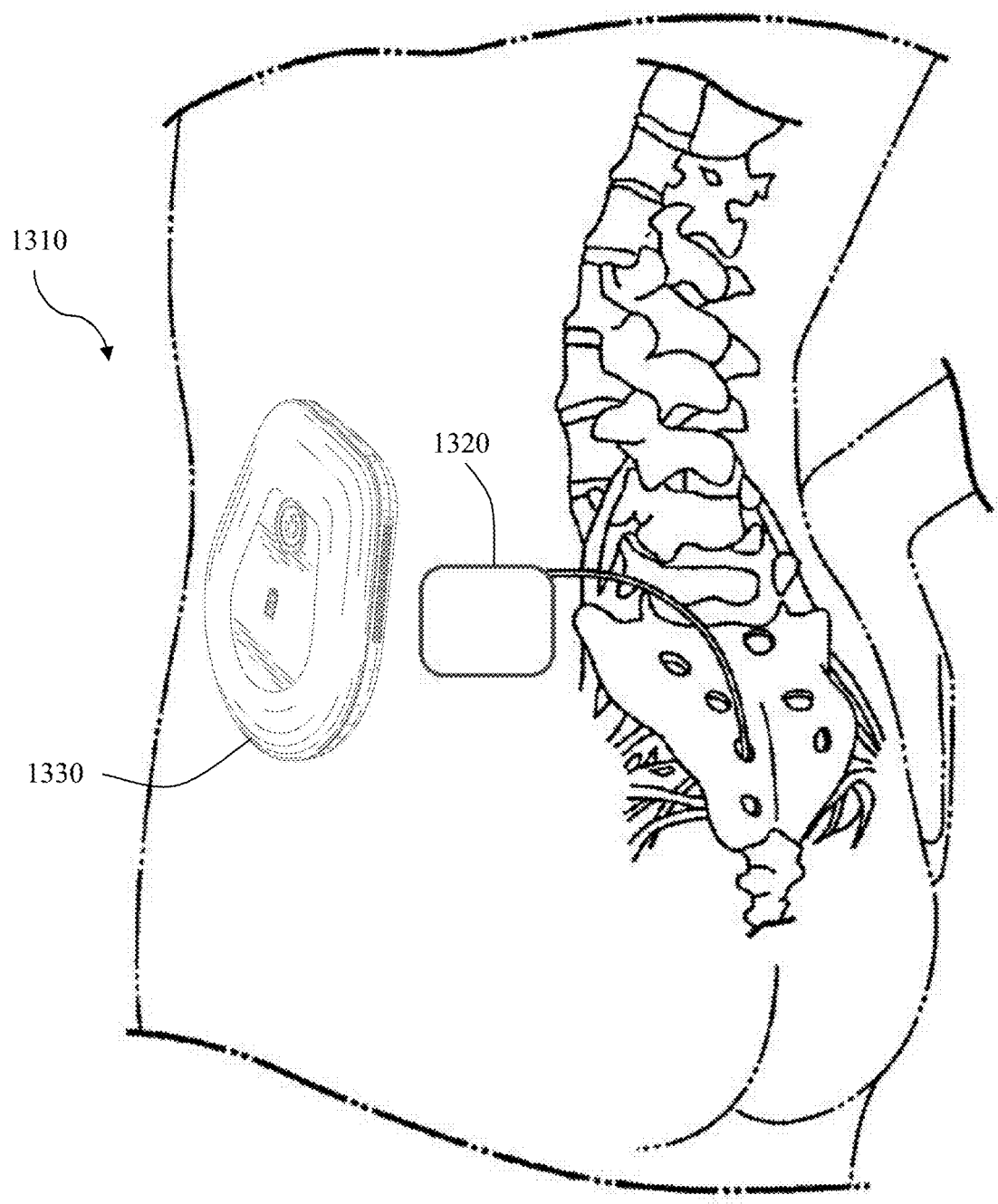
FIG. 13A is a schematic of a sacral nerve stimulation system according to an embodiment.
Figure 13B:
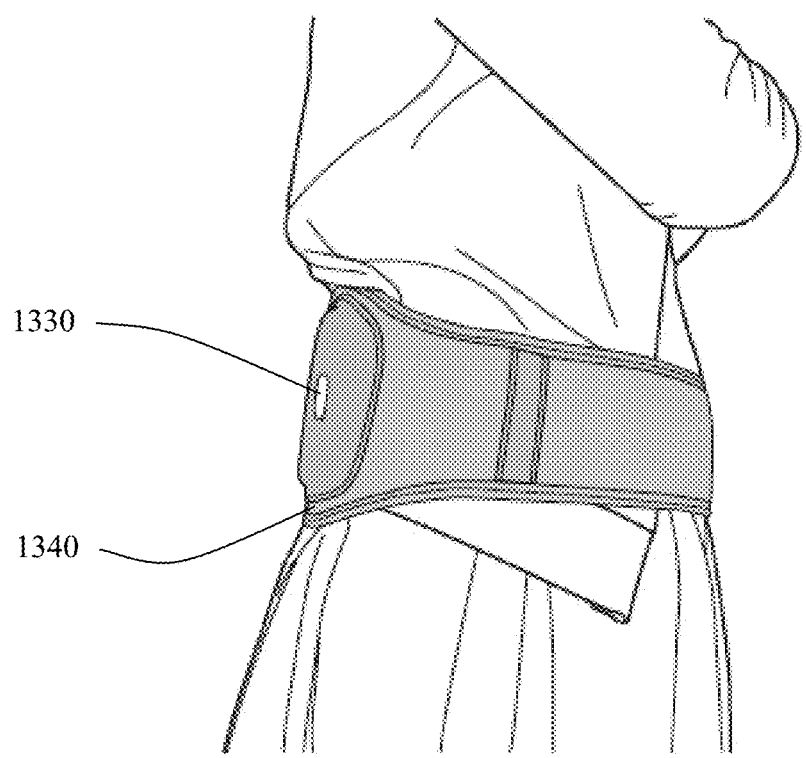
FIG. 13B is a schematic of a sacral nerve stimulation system with a wearable belt according to an embodiment.

In an example, embodiments of the present disclosure may be used as part of a system for treating pelvic health conditions including incontinence, overactive bladder, pelvic pain or other pelvic floor disorders. Referring to FIGS. 13A-B, embodiments of the present disclosure can be implemented as part of a sacral nerve stimulation system 1310, including a rechargeable implantable nerve stimulation device 1320 and an external recharger 1330, wherein external recharger 1330 can be positioned on or proximate to skin of the patient over the location of implantable nerve stimulation device 1320 to facilitate recharging. Referring to FIG. 13B, external recharger 1330 may also be wearable on the patient such as with a belt 1340.

Figure 14:
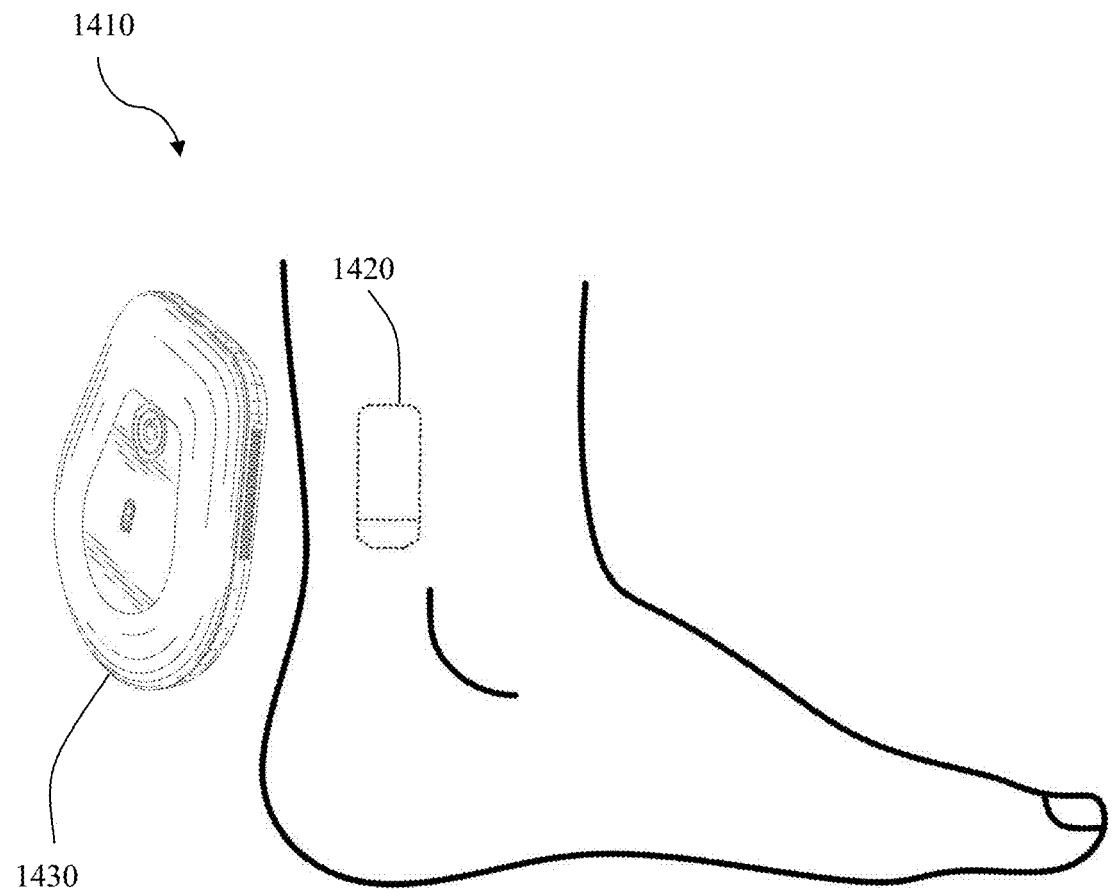
FIG. 14 is a schematic of a tibial nerve stimulation system according to an embodiment.

Referring to FIG. 14, in another example pertaining to treatment of pelvic health disorders, embodiments of the present disclosure may be implemented as part of a tibial nerve stimulation system 1410, including an implantable tibial nerve stimulation device 1420 and an external recharger 1430, wherein external recharger 1430 can be positioned on or proximate to skin of the patient over the location of implantable nerve stimulation device 1420 to facilitate recharging. Tibial nerve stimulation system 1410 may also include a wearable ankle cuff to hold external recharger 1430 in position on an ankle of a patient.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A device for remote charging, the device comprising:
a plurality of charging coils;
a power supply coupled to all of the plurality of charging coils;
a switch matrix connecting the power supply to the plurality of charging coils such that a first subset of the plurality of charging coils associated with a first charging zone are powered and a second subset of the plurality of charging coils associated with a second charging zone are powered; and
a processor configured to define the first subset of the plurality of charging coils based upon a received charge current, a threshold, and a level of hysteresis, and further configured to define the second subset of the plurality of charging coils based upon the received charge current, the threshold, and the level of hysteresis.

2. The device of claim 1, wherein the threshold is preset based upon a corresponding implantable device to be charged by the device for remote charging.

3. The device of claim 1, wherein the threshold is based upon a historical average charge current from prior charging sessions of a particular corresponding implantable device.

4. The device of claim 1, wherein the plurality of charging coils are arranged in a cloverleaf pattern.

5. The device of claim 1, wherein the plurality of charging coils comprises more than four charging coils.

6. The device of claim 1, wherein the plurality of charging coils are arranged in a series of rows and in a series of columns.

7. A system comprising:
an implantable medical device defining a depth and an angle of orientation with respect to a device for remote charging;
the device for remote charging, including:
a plurality of charging coils;
a power supply coupled to all of the plurality of charging coils;
a switch matrix connecting the power supply to the plurality of charging coils such that a first subset of the plurality of charging coils associated with a first charging zone are powered and a second subset of the plurality of charging coils associated with a second charging zone are powered; and
a processor configured to define the first subset of the plurality of charging coils based upon a received charge current, a threshold, and a level of hysteresis, and further configured to define the second subset of the plurality of charging coils based upon the received charge current, the threshold, and the level of hysteresis,
wherein the processor is configured to select the first subset of the plurality of charging coils or the second subset of the plurality of charging coils based upon the depth and the angle of orientation of the implantable medical device.

8. The system of claim 7, wherein the threshold is preset based upon the implantable device to be charged by the device for remote charging.

9. The system of claim 7, wherein the threshold is based upon a historical average charge current associated with the implantable device.

10. The system of claim 7, wherein the plurality of charging coils are arranged in a cloverleaf pattern.

11. The system of claim 7, wherein the plurality of charging coils comprises more than four charging coils.

12. The system of claim 7, wherein the plurality of charging coils are arranged in a series of rows and in a series of columns.

* * * * *